United States Patent
Zhang

(10) Patent No.: US 9,585,926 B2
(45) Date of Patent: Mar. 7, 2017

(54) ASTRAGALUS SEED EXTRACT SOLUTION AND ITS USE FOR TREATING SKIN DISORDERS AND CONDITIONS

(71) Applicant: Nefeli Corporation, Port Washington, NY (US)

(72) Inventor: Ping Zhang, Port Washington, NY (US)

(73) Assignee: Nefeli Corporation, Port Washington, NY (US)

( * ) Notice: Subject to any disclaimer, the term of this patent is extended or adjusted under 35 U.S.C. 154(b) by 23 days.

(21) Appl. No.: 14/456,638

(22) Filed: Aug. 11, 2014

(65) Prior Publication Data

US 2014/0348964 A1 Nov. 27, 2014

Related U.S. Application Data

(62) Division of application No. 13/723,602, filed on Dec. 21, 2012, now abandoned.

(60) Provisional application No. 61/579,726, filed on Dec. 23, 2011.

(51) Int. Cl.
| | | |
|---|---|---|
| *A61K 36/48* | (2006.01) | |
| *A61K 36/481* | (2006.01) | |
| *A61K 8/97* | (2006.01) | |
| *A61Q 19/08* | (2006.01) | |
| *A61Q 19/00* | (2006.01) | |
| *A61Q 19/02* | (2006.01) | |

(52) U.S. Cl.
CPC .............. *A61K 36/481* (2013.01); *A61K 8/97* (2013.01); *A61Q 19/00* (2013.01); *A61Q 19/02* (2013.01); *A61Q 19/08* (2013.01)

(58) Field of Classification Search
None
See application file for complete search history.

(56) References Cited

FOREIGN PATENT DOCUMENTS

| JP | 2005220100 A | 8/2005 |
|---|---|---|
| JP | 2005320271 A | 11/2005 |
| KR | 100844516 B1 | 7/2008 |
| KR | 20090083082 | 8/2009 |
| KR | 20090083083 | 8/2009 |
| KR | 20090111679 A | 10/2009 |
| KR | 20100071730 A | 6/2010 |
| KR | 20110017563 A | 2/2011 |

OTHER PUBLICATIONS

Lim et al. (2011) Journal of Industrail and Engineering Chemistry 17: 510-516.*
Teo et al "Pressurized Hot Water Extraction (PHWE)" Journal of Chromatography A vol. 1217, pp. 2484-2494. 2010.
Qi et al "Protective Effect of Flavonoids from *Astragalus complanatus* on Radiation Induced Damages in Mice" Fitoterapia vol. 82, pp. 383-392. 2011.
Kim et al "Antioxidant Activities of Hot Water Extracts from Various Spices" International Journal of Molecular Sciences vol. 12, pp. 4120-4131. 2011.
Website document entitled "Chinese Herb Tea" http://en.wikipedia.org/wiki/chinese_herb_tea.

* cited by examiner

*Primary Examiner* — Chris R Tate
*Assistant Examiner* — Russell Fiebig
(74) *Attorney, Agent, or Firm* — Cesari and McKenna, LLP

(57) ABSTRACT

Described is a method of treating a skin condition in a subject. The method includes applying topically to the subject an effective amount of an aqueous *Astragalus* seed extract solution to a skin area in need of reducing or slowing the skin condition. The aqueous *Astragalus* seed extract solution is prepared by a procedure including the steps of: soaking dried seeds of *Astragalus* seed in an aqueous solvent to form a suspension; boiling the suspension for at least 30 minutes; and filtering the suspension so as to obtain the *Astragalus* seed aqueous extract solution, the weight ratio of the dried seeds of *Astragalus* seed to the extract solution being 1:100 to 75:100.

13 Claims, No Drawings

ASTRAGALUS SEED EXTRACT SOLUTION AND ITS USE FOR TREATING SKIN DISORDERS AND CONDITIONS

CROSS-REFERENCE TO RELATED APPLICATIONS

This is a divisional application of U.S. patent application Ser. No. 13/723,602, filed on Dec. 21, 2012, which claims priority to U.S. Provisional Patent Application No. 61/579,726, filed on Dec. 23, 2011. The contents of all prior applications are incorporated by reference herein in their entirety.

BACKGROUND

*Astragalus* is a large genus that contains about 3000 different species, including *Astragalus* seed, also called Flatstem milkvetch seed or *Astragalus complanatus*.

*Astragalus* seed is widely grown in northern China. According to traditional Chinese medicine, it is efficacious in improving vision, liver functions, and kidney functions. However, its use in skin care has not been reported.

There are many skin care products for treating skin disorders and conditions, such is as acne and age spots. Chemical ingredients in many of these products are irritating or even harmful to the skin. There is a need for natural skin care products that have no side effects.

SUMMARY

In one aspect, this invention features an aqueous *Astragalus* seed extract solution prepared by a method including: (1) soaking dried seeds of *Astragalus* seed in an aqueous solution to form a suspension, (2) boiling (e.g., 100° C. or above at 1 atm) the suspension for at least 30 minutes, and (3) filtering the suspension so as to obtain the *Astragalus* seed aqueous extract solution, in which a weight ratio of the dried *Astragalus* seed to the extract solution is 1:100 to 75:100 (preferably 8:100 to 50:100 and more preferably 10:100 to 25:100). The term "an aqueous solvent" herein refers to water itself or a solvent mixture that contains water at least 15% (e.g., 50%, 75% or 90%) by weight, and the remaining of the solution can be, but is not limited to, vinegar, alcohol, or any other herbal extraction solvent. Preferably, *Astragalus* seed is the only herb used in the above-described method. The method can further include, after the filtering step, a step of adjusting the weight ratio by boiling the extract solution to decrease its volume or by adding to the extract solution a solvent to increase its volume to form an aqueous *Astragalus* seed extract solution of this invention.

In one embodiment, the dried seeds of *Astragalus* seed are crushed or ground in the suspension after the boiling step while the suspension remains at an elevated temperature. In that case, the suspension containing the crushed or ground seeds is preferably boiled again for a period of time. As another alternative, they can be crushed or ground right after the soaking step and before the boiling step.

In another aspect, this invention features a skin care composition containing the above-described aqueous *Astragalus* seed extract solution and a non-aqueous skin acceptable carrier, in which the extract solution is 0.01-75% by weight (preferably 0.5-50% by weight and more preferably 10-25% by weight).

In still another aspect, this invention features a skin care method. The method includes applying topically an effective amount of the above-described aqueous *Astragalus* seed extract solution to a skin area in need of reducing or slowing one or more skin disorders or conditions (i.e., unrelated to aging), e.g., acne, acne marks, scars, rosacea, irritated skin, dark spots, enlarged skin pores, and blemishes.

In yet another aspect, this invention features another skin care method. The method includes applying topically an effective amount of the above-described aqueous *Astragalus* seed extract solution to a skin area in need of reducing or slowing one or more skin conditions (i.e., related to aging), e.g., wrinkles, loose skin, sagging, uneven skin tone, dull complexion, and age spots.

The details of one or more embodiments of the invention are set forth in the description below. Other features, objects, and advantages of the invention will be apparent from the description, the examples, and the claims below.

DETAILED DESCRIPTION

This invention is based on the discovery that an aqueous *Astragalus* seed extract solution can be applied to a skin area to reduce or slow a skin disorder or a skin condition.

Examples of skin disorders or conditions (i.e., unrelated to aging) include, but are not limited to, acne, acne marks, scars, rosacea, irritated skin, dark spots, and blemishes.

Acne affects the skin's oil glands. In particular, a pimple grows when a follicle of a skin gland clogs up. More specifically, the hair, sebum, and skin cells clump together to form a plug, and when the plug starts to break down, a pimple grows. Acne can be caused by heredity, medications, greasy cosmetics, hormonal changes during pregnancy, puberty, menstrual periods, stress, and the use or termination of birth control pills.

Acne marks, i.e., red or hyper pigmented marks on the skin, can appear after acne is healed. The redness or hyperpigmentation can take 6-12 months to go through a healing process if no further acne occurs in that area. However, a permanent scar or a defect is possible in the skin area where acne occurred.

Scars are areas of fibrous tissues that replace normal skin after injury. They result from a healing process of wound repair in the skin.

Rosacea does not only cause redness and pimples on the nose, cheeks, chin, and forehead, it also causes small visible blood vessels on the face and dry and red irritated eyes. Sometimes redness lasts for days. The causes of rosacea are not known but it tends to affect people who have fair skin or blush easily.

Irritated skin refers to skin that is itchy and may also be red, scaly, dry, flaky, swollen, or blistered. It can be caused by many factors such as eczema, psoriasis, chemicals, environmental conditions, expired cosmetics, and allergens.

Dark spots and blemishes, also called "hyperpigmentation," can be induced by various factors, such as intrinsic aging-related causes (e.g., menopause, hormonal changes), extrinsic aging-related causes (e.g., photoaging), and factors not related to aging, e.g., pregnancy, medications, certain diseases (e.g., lupus, liver disease, Addison's disease, and pituitary tumors), and hormonal changes.

Examples of skin conditions (i.e., related to aging) include, but are not limited to, wrinkles, loose skin, sagging, uneven skin tone, dull complexion, and age spots.

Aging of the skin results from a combination of multiple factors including intrinsic factors (e.g., slow collagen production) and extrinsic factors (e.g., sun damage or smoking). It takes place at a microscopic or biochemical level, but manifests outwardly as wrinkles, dryness, roughness or dullness, sagging, and other signs.

The aqueous *Astragalus* seed extract solution of this invention can be prepared by multiple procedures. For example, an aqueous *Astragalus* seed extract solution can be prepared by a method including: (1) soaking dried seeds of *Astragalus* seed in an aqueous solution to form a suspension, (2) boiling the suspension at 100° C. or above at 1 atm for at least 30 minutes, and (3) filtering the suspension so as to obtain the *Astragalus* seed aqueous extract solution.

In one embodiment, the boiled suspension can be crushed in a blender for 30 seconds, reheated to a boil, and simmered on low heat for another 30 minutes.

In another embodiment, the suspension can be crushed in a blender for a second time for 30 seconds after the second simmering step.

In a particular embodiment, the suspension can be filtered through a filter cloth to remove insoluble sediment. Additionally, the filter cloth containing the sediment can be squeezed to extract additional liquid. Advantageously, the squeezed filter cloth can be dipped into the extracted liquid and squeezed again so as to increase the yield of the extract. In another embodiment, the filtering step can be repeated several times. In a preferred embodiment, the extract can be concentrated by boiling to obtain an *Astragalus* seed extract solution in which the weight ratio of the dried seeds to the extract solution is 10:100.

The procedure for obtaining the *Astragalus* seed aqueous extract solution can also include the steps of pressure cooking of a suspension of the seeds or infusing the seeds in alcohol or oil.

An effective amount of an aqueous *Astragalus* seed extract solution obtained by the above methods can be applied topically to a skin area in need of reducing or slowing a skin disorder (i.e., unrelated to aging) or a skin condition (i.e., related to aging). The beneficial effects are obtained over a period of time.

Also within the scope of this invention is a skin care composition that contains an aqueous *Astragalus* seed extract solution and a non-aqueous skin acceptable carrier. The extract solution is 0.01-75% by weight. The non-aqueous skin acceptable carrier can be an excipient, a vehicle, or a media for topical administration. In a preferred embodiment, the skin care composition contains one or more other ingredients known to have a beneficial effect on the skin, including, but not limited to, sunscreens, vitamins, oils, or herbal extracts (e.g., extracted from fermentation or other methods).

In one embodiment, an aqueous *Astragalus* seed extract solution of this invention can be fermented with rice and then combined with a non-aqueous or aqueous carrier for skin care.

The skin care composition of this invention can also contain other ingredients that are typically found in a cosmetic formulation including, but not limited to, pigments, perfumes, and preservatives. The types and amounts of ingredients other than the aqueous *Astragalus* seed extract solution can be determined by an ordinary artisan based on general knowledge in the skin care industry.

The skin care composition of this invention can also include one or more materials typically applied to the skin for treatment. They include, but are not limited to cream, moisturizer, lotion, gel, mask, spray, and serum.

The specific examples below are to be construed as merely illustrative, and not limitative of the remainder of the disclosure in any way whatsoever. Without further elaboration, it is believed that one skilled in the art can, based on the description herein, utilize the present invention to its fullest extent.

EXAMPLE 1

Preparation of an Aqueous *Astragalus* Seed Extract Solution

Ten grams of dried seeds of *Astragalus* seed were gently washed and then soaked in 1500 g of water for 30 minutes. The thus-obtained suspension was heated to a boil for approximately 5 minutes and then simmered on low heat for 30 minutes. The suspension was removed from the heat source and crushed in a blender for 30 seconds. After crushing, the suspension was reheated to a boil and then simmered on low heat for another 30 minutes. The suspension was removed from the heat source and again crushed in a blender for 30 seconds. After crushing, the suspension was reheated to a boil and then simmered on low heat for another 30 minutes. It was then cooled to room temperature. The suspension was filtered through a filter cloth to remove insoluble sediment. The filter cloth containing the sediment was squeezed so as to extract additional liquid. To increase yield, the squeezed filter cloth was dipped into the extracted liquid and squeezed again so as to extract more of the herbal liquid. The filtering step can be repeated several times. The remaining liquid was concentrated by boiling to obtain an *Astragalus* seed extract solution in which the weight ratio of the dried seeds to the extract solution is 10:100.

EXAMPLE 2

Alternative Method for Preparing an Aqueous *Astragalus* Seed Extract Solution

Gently wash 10 g of dried seeds of *Astragalus* seed. Soak the seeds in 1500 g of water for 30 minutes. The thus-obtained suspension is heated to a boil for approximately 5 minutes, then simmered on low heat for 30 minutes. The suspension is removed from the heat source and crushed in a blender for 30 seconds. Then, the suspension is brought to a boil again and simmered for another 5 minutes. After simmering the suspension is cooled to room temperature and then filtered through a filter cloth to remove insoluble sediment. The filter cloth containing the remaining sediment is squeezed to extract more liquid. The filter cloth containing the sediment is then dipped in the extracted liquid and squeezed again to extract additional liquid. This step can be repeated several times. The remaining liquid can be concentrated by boiling or diluted by addition of water to obtain 100 g of an *Astragalus* seed extract solution, in which the weight ratio of the dried seeds to the extract solution is 10:100.

EXAMPLE 3

Another Alternative Method for Preparing an Aqueous *Astragalus* Seed Extract Solution Gently wash 10 g of dried seeds of *Astragalus* seed and soak the seeds in 1500 g of water for 30 minutes. The thus-obtained suspension is heated to a boil for approximately 5 minutes and then simmered on low heat for 30 minutes. The suspension is removed from the heat source and crushed in a blender for 30 seconds. The suspension is then brought to a boil again and simmered for another 30 minutes. The suspension is removed from the heat source and again crushed in a blender for 30 seconds. The suspension is again brought to a boil and simmered for another 5 minutes, then cooled to the room temperature. The suspension is filtered through a filter cloth to remove insoluble sediment. The filter cloth containing the remaining sediment is squeezed to extract more liquid. The filter cloth containing the sediment is then dipped in the extracted liquid and squeezed again to extract more of the herbal liquid. This step can be repeated several times. The remaining liquid can be concentrated by boiling or diluted by addition of water to obtain 100 g of an *Astragalus* seed extract solution, in which the weight ratio of the dried seeds to the extract solution is 10:100.

EXAMPLE 4

Additional Method for Preparing an Aqueous *Astragalus* Seed Extract Solution

Gently wash 10 g of dried seeds of *Astragalus* seed and soak the seeds in 1500 g of water for 30 minutes. The thus-obtained suspension is heated to a boil for approximately 5 minutes and then simmered on low heat for 60 minutes. The suspension is cooled to room temperature and then filtered through a filter cloth to remove insoluble sediment. The filter cloth containing the remaining sediment is squeezed to extract more liquid. The filter cloth containing the sediment is then dipped in the extracted liquid and squeezed again to extract more of the herbal liquid. This step can be repeated several times. The remaining liquid can be concentrated by boiling or diluted by addition of water to obtain 100 g of an *Astragalus* seed extract solution, in which the weight ratio of the dried seeds to the extract solution is 10:100.

EXAMPLE 5

Another Embodiment of a Method for Preparing an Aqueous *Astragalus* Seed Extract Solution Gently wash 10 g of dried seeds of *Astragalus* seed and soak the seeds in 1500 g of water for 30 minutes. The thus-obtained suspension is crushed in a blender for 30 seconds. The suspension is heated to a boil for approximately 5 minutes, simmered on low heat for 30 minutes, and cooled to room temperature. The suspension is then filtered through a filter cloth to remove insoluble sediment. The filter cloth containing the remaining sediment is squeezed to extract more liquid. The filter cloth containing the sediment is then dipped in the extracted liquid and squeezed again to extract more of the herbal liquid. This step can be repeated several times. The remaining liquid can be concentrated by boiling or diluted by addition of water to obtain 100 g of an *Astragalus* seed extract solution, in which the weight ratio of the dried seeds to the extract solution is 10:100.

EXAMPLE 6

Topical Administration of an Aqueous *Astragalus* Seed Extract Solution

A 42 year old female patient presented with acne, acne marks on her face, wrinkles in the frown area, and extensive dark spots caused by sun damage. These symptoms had persisted for about 2 years.

Clinical examination noted dark spots appearing mainly on her forehead, especially in the center of the forehead near the eyebrows, cheek area, and upper lip area. Also observed were wrinkles in the frown area, acne and acne marks, and blemishes on the forehead, the lower part of the cheeks, and around the mouth. Additionally, enlarged skin pores and black heads around the T-zone area were observed.

The patient was treated with a 6% aqueous extract solution of *Astragalus complanatus*. The extract was applied twice daily, with 10 drops applied in the morning and 10 drops applied in the evening after cleaning the face.

Following treatment for 2.5 weeks, the patient reported a reduction in wrinkles, dark circles, age spots and discolorations, acne, acne marks, dark spots, blemishes, and dull skin. The patient also reported improved suppleness, skin texture, radiance, and a reduced occurrence of blackheads.

Clinical observations included a significant lightening of dark spots on the patient's forehead. Acne scars on the right side of her forehead were diminished in color and size. Frown wrinkles were shortened and thinner. A significant lightening of dark spots on the bridge of her nose was observed. Also observed was a significant diminishment of acne, blemishes, and dark spots on the left side of the face. An acne scar under the right eye was diminished in color and size. Additionally, pores were diminished in size, particularly on the nose. There was an overall improvement in radiance and complexion.

EXAMPLE 7

Treatment of Age Spots With an Aqueous *Astragalus* Seed Extract Solution

A 48 year old female patient complained of age spots on the face and redness on her left cheek.

Clinical observations included dark spots on the cheeks and around nasal area, redness on the left cheek, and enlarged pores on the nose.

The patient was treated with a 6% aqueous extract solution of *Astragalus complanatus*. The extract was applied twice daily to the left side of the face, with 5 drops applied in the morning and 5 drops applied in the evening after cleaning the face.

After 3 weeks of treatment, the patient reported lightening of dark spots, less redness, and a significant reduction in pore size.

Upon examination, the left cheek demonstrated significantly reduced redness and diminished dark spots. On the nose, pores were diminished in size, and dark spots were to diminished in appearance.

EXAMPLE 8

Treatment of Acne With an Aqueous *Astragalus* Seed Extract Solution

A 13 year old male presented with acne breakouts. Acne blemishes were particularly severe on the forehead. Redness was also observed on the cheeks and surrounding the nose.

The patient was treated with a 6% aqueous extract solution of *Astragalus complanatus*. The extract was applied twice daily, with 10 drops applied in the morning and 10 drops applied in the evening after cleaning the face.

After 2 weeks of treatment, the patient reported a significant reduction in acne breakouts on his forehead.

A clinical evaluation after 7.5 weeks of treatment demonstrated a dramatic reduction of acne and acne marks on the forehead.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

The invention claimed is:

1. A method of treating a skin condition in a subject, the method comprising topically applying a composition comprising an effective amount of an aqueous *Astragalus complanatus* extract solution to an area of skin in need thereof,
wherein the skin condition is selected from the group consisting of acne, acne scars and hyperpigmentation,
wherein the aqueous *Astragalus complanatus* extract solution is prepared by a procedure comprising the steps of:
(a) soaking dried *Astragalus complanatus* seeds in an aqueous solvent to form a suspension,
(b) boiling the suspension for at least 30 minutes, and
(c) filtering the boiled suspension to obtain the aqueous *Astragalus complanatus* extract solution,
wherein the weight ratio of the dried *Astragalus complanatus* seeds to the aqueous solvent is 1:100 to 75:100.

2. The method of claim 1, wherein the weight ratio of the dried *Astragalus complanatus* seeds to the aqueous solvent is 8:100 to 50:100.

3. A method of claim 2, wherein the weight ratio of the dried *Astragalus complanatus* seeds to the aqueous solvent is 10:100 to 25:100.

4. The method of claim 1, wherein the procedure for preparing the aqueous *Astragalus complanatus* extract solution further includes, after the filtering step, adjusting the weight ratio of the extract solution by boiling the extract solution to decrease its volume or by adding to the extract solution a solvent to increase its volume.

5. The method of claim 4, wherein the weight ratio of the dried *Astragalus complanatus* seeds to the aqueous solvent is 10:100 to 25:100.

6. The method of claim 1, wherein the composition is applied daily.

7. The method of claim 1, wherein the composition contains 0.01-75% by weight of the aqueous *Astragalus complanatus* extract solution and a non-aqueous skin acceptable carrier.

8. The method of claim 7, wherein the composition contains 0.5-50% by weight of the extract solution.

9. The method of claim 8, wherein the composition contains 10-25% by weight of the extract solution.

10. The method of claim 9, wherein the weight ratio of the dried *Astragalus complanatus* seeds to the aqueous solvent is 10:100 to 25:100.

11. The method of claim 7, wherein the composition is a cream, moisturizer, lotion, gel, mask, spray, or serum.

12. The method of claim 1, wherein the composition consists of 0.01-75% by weight of the aqueous *Astragalus complanatus* extract solution and one or more ingredients selected from the group consisting of a non-aqueous skin acceptable carrier, a sunscreen, a vitamin, a pigment, a perfume, and a preservative.

13. The method of claim 12, wherein the composition is a cream, moisturizer, lotion, gel, mask, spray, or serum.

* * * * *